United States Patent [19]

Casale et al.

[11] Patent Number: 5,214,219
[45] Date of Patent: May 25, 1993

[54] METHOD OF HYDROGENATING GLYCEROL

[75] Inventors: Bruno Casale, Novara; Ana Maria Gomez, Torino, both of Italy

[73] Assignee: Novamont S.p.A., Milan, Italy

[21] Appl. No.: 911,133

[22] Filed: Jul. 9, 1992

[30] Foreign Application Priority Data

Jul. 10, 1991 [IT] Italy .................. T091A000537

[51] Int. Cl.$^5$ .......................................... C07C 29/132
[52] U.S. Cl. ............................................ 568/861
[58] Field of Search ................................ 568/861

[56] References Cited

U.S. PATENT DOCUMENTS 4,960,960 10/1990 Harrison et al. .................. 568/861
5,120,885 6/1992 Tsukada et al. .................. 568/885

FOREIGN PATENT DOCUMENTS 072629 7/1982 European Pat. Off. .

Primary Examiner—Marianne M. Cintins
Assistant Examiner—Rebecca Cook
Attorney, Agent, or Firm—Elizabeth M. Barnhard; Bryan Cave

[57] ABSTRACT

A catalytic method of hydrogenating glycerol is directed essentially towards the production of oxygenated compounds having from 1 to 3 carbon atoms, mainly 1, 2 propandiol and 1, 2 ethandiol. It provides for glycerol to be reacted with hydrogen in the presence of a catalyst including copper and zinc at a temperature of at least 220° C.

7 Claims, No Drawings

METHOD OF HYDROGENATING GLYCEROL

The present invention relates to a method of hydrogenating glycerol, particularly in order to produce industrially useful oxygenated compounds of greater commercial value.

The saponification and transesterification of fats in order to produce fatty acids or methyl esters thereof lead to the production of large quantities of impure glycerol which is normally considered to be a byproduct since it requires expensive purification processes in order to be used further.

On the other hand, the known methods of converting purified glycerols by hydrogenation are unattractive from an industrial point of view.

German patent DE-PS-541362 describes the hydrogenation of glycerol with a nickel-based catalyst to form 1,2-propandiol. Tests carried out by the Applicant have shown that, with the use of nickel as the catalyst, satisfactory yields of glycerol conversion can be achieved only at high temperatures of about 270° C., at which temperatures considerable quantities of unwanted gaseous hydrocarbons, mainly methane, are produced.

European patent application EP-A-72629 describes a catalytic method of hydrogenating polyols, including glycerol, with the use of usual hydrogenation catalysts, for example, nickel, platinum or palladium. According to this document, a key factor for achieving high polyol-conversion rates and selectivity towards the formation of oxygenated compounds, particularly 1,2-ethandiol and propandiol, is the presence, together with the reagents and the catalyst, of a promoter constituted by one of the basic inorganic hydroxides or a mixture thereof.

The object of the present invention is to provide a method which enables glycerol, particularly impure glycerol produced as a byproduct of processes for the saponification (or transesterification) of fats, to be converted with high yields and good overall selectivity towards the production of oxygenated compounds.

Within the scope of the present invention, it has been discovered that this object is achieved by the hydrogenation of glycerol with the use of a copper-zinc catalyst.

The subject of the present invention is therefore a method of hydrogenating glycerol in order, essentially, to produce oxygenated compounds having from one to three carbon atoms, in which the glycerol is placed in contact with hydrogen and made to react therewith in the presence of a copper-zinc catalyst, at a temperature of at least 200° C.

It has been found that, under these process conditions, the reaction product is constituted mainly by 1,2-propandiol.

The method of the invention enables satisfactory glycerol-conversion rates and selectivity towards the formation of oxygenated compounds to be achieved without the need to add reagents for promoting or moderating the activity of the catalyst. This brings the advantage that the method is simpler to carry out, with fewer parameters to be kept under control, in addition, of course, to the fact that there is no need to provide these reagents.

The method of the invention may also be carried out with the use of glycerol resulting from the saponification or transesterification of fats, without the need to use particularly complicated or expensive processes to purify it. Simple separation techniques (passage through an ion-exchange resin) provide glycerol which reacts to give conversion rates and selectivities close to those of pure glycerol and the process can therefore be integrated within a process for the saponification or transesterification of fats to produce industrially useful final products of a high commercial value.

The copper-zinc catalyst used may be a commercial catalyst constituted by a copper oxide/zinc oxide mixture, preferably with alumina.

As will become clear from the experimental data given below, the best glycerol-conversion results are achieved when the atomic ratio between the copper and the zinc in the catalyst is between 0.2 and 6 and preferably between 0.5 and 3.

The operative conditions required for the reaction are a reaction temperature higher than 200° C., preferably of between 220° and 280° C., and most preferably of between 230° and 265° C., and a total pressure of between 5 and 20 MPa, preferably of between 10 and 15 MPa. In the case of batch reactions, the concentration of the catalyst is generally between about 2.5 and 10% of the weight of the glycerol and preferably from 4 to 5% by weight.

The glycerol is preferably supplied to the hydrogenation reactor in aqueous solution at concentrations generally of between 20 and 60% by weight, preferably of from 30 to 40% by weight.

It is also possible, however, to use nonaqueous solvents in which glycerol is at least partially soluble, under the reaction conditions, and which do not interfere with the hydrogenation reaction. These solvents include polar solvents, particularly alcohols such as methanol, ethanol and propanol.

The invention will now be described in greater detail on the basis of the following Examples 1 to 16.

EXAMPLES 1–10

These tests were carried out discontinuously using, as the reactor, a 500 cm$^3$ Brignole autoclave with a magnetic stirring system having a stirrer with four radial blades and four washplates.

The method of operation followed provided for the autoclave to be loaded with about 250 cm$^3$ of an aqueous solution of glycerol of a predetermined concentration with the desired quantity of the catalyst. In tests 1-9, glycerol of reagent purity was used, but in test 10 crude glycerol which came from a plant for the hydrolysis of fats and had been pre-treated on an ion-exchange resin was used. The autoclave was then closed and flushed with hydrogen several times to eliminate all the air present. The autoclave was then pressurised with hydrogen to 100 bars, heated to the desired reaction temperature, and kept under these conditions for two hours. At the end of this period, the autoclave was cooled to ambient temperature and a gas sample was withdrawn under these conditions. The autoclave was then brought to atmospheric pressure and opened to enable the reaction liquid to be discharged, weighed, filtered to separate the catalyst, and analysed.

The liquid was analysed by high-performance liquid chromatography (HPLC) in a Waters Model 411 chromatograph with an Aminex HPX 87H column and a refractive index detector.

The gas was analysed by gas chromatography in a Carlo Erba Fractovap Model C-ATC/F chromatograph with a silica gel column, operating at 50° C. with a thermal conductivity detector.

Table I summarises the process conditions as regards the temperature, the atomic ratio between the copper and the zinc in the catalyst, the ratio between the weight of the catalyst and the weight of glycerol, and the concentration of the glycerol, as well as the results of the tests carried out as regards the conversion rates and selectivities. The conversion rate is expressed as the ratio, in percentage terms, between the glycerol converted and the glycerol supplied, and the selectivity towards the various reaction products is expressed as the ratio, in percentage terms, between the glycerol converted into the product under consideration and the total glycerol converted. Due to inevitable experimental and analytical errors, the sums of the selectivities towards the various products do not give values of 100, but give slightly higher or lower values.

The symbols used in Table I and in the subsequent Table II, have the following meanings:
PG: 1,2-propandiol
EG: 1,2- ethandiol
AL: lactic acid
MeOH: methanol
EtOH: ethanol
PrOH: n-propanol
Gas: $CH_4 + CO + CO_2$
A: alcohols 96% was achieved with selectivity towards propandiol even greater than 85% (Example 10).

EXAMPLES 11–16

These tests were carried out continuously with the use of a tubular reactor having an inside diameter of about 2 cm and containing 100 cm$^3$ of catalyst.

The catalyst used was a copper oxide/zinc oxide/alumina catalyst of a type available commercially, supplied in the form of ¼" extruded cylinders with an atomic ratio of 0.89 between the copper and the zinc.

The reactor was loaded by the introduction first of a 2.5 cm layer of ¼" ceramic Berl saddles, then the required volume of the catalyst and, finally, a second 2.5 cm layer of ¼" Berl saddles.

The catalyst thus loaded was first activated by the supply of a stream of 100% nitrogen to the reactor with heating so that both the gas admitted and the reactor were at a temperature of 130°. When these conditions had been achieved, the stream of nitrogen was replaced by a stream including 96% by volume of nitrogen and 4% by volume of hydrogen, in order to reduce to the metallic state all the copper present as oxides. At this stage, it was noted that there was a local temperature rise due to the exothermal nature of the reduction reaction, and that water was formed. During this operation,

TABLE I

| Example N° | T (°C.) | Cu/Zn Ratio | Cat./glycerol Ratio (%) | glycerol concentr. (g/l) | Conversion % | SELECTIVITY % | | | | | | |
|---|---|---|---|---|---|---|---|---|---|---|---|---|
| | | | | | | EG | PG | AL | MeOH | EtOH | PrOH | Gas |
| 1 | 270 | 0.89 | 5 | 300 | 99.4 | 6 | 84.4 | 0.3 | 1.9 | 0.08 | 1.9 | 1.3 |
| 2 | 270 | 1.5 | 5 | 300 | 99.9 | 6.4 | 80.8 | 0.15 | 1.8 | 0.2 | 4.4 | 2 |
| 3 | 270 | 5.5 | 5 | 300 | 91.1 | 4.9 | 85.1 | 0.3 | 1.2 | — | 1.7 | 1.3 |
| 4 | 240 | 0.89 | 5 | 300 | 60 | 4.7 | 93.1 | 0.07 | 0.6 | — | 0.35 | 1.3 |
| 5 | 270 | 0.89 | 5 | 200 | 98.7 | 5.9 | 83 | 0.09 | 1.9 | 0.17 | 4.0 | 1.6 |
| 6 | 270 | 0.89 | 5 | 400 | 99.4 | 5.0 | 79.5 | 0.4 | 3.9 | 0.16 | 6.4 | 1.7 |
| 7 | 270 | 0.89 | 1 | 300 | 8.3 | 5.4 | 97.5 | 4.4 | 1.9 | — | 10 | 0.4 |
| 8 | 270 | 0.89 | 2.5 | 300 | 82 | 5.1 | 85.7 | 0.3 | 1.8 | — | 4.8 | 1.2 |
| 9 | 270 | 0.89 | 10 | 300 | 99.8 | 5.5 | 80 | 0.5 | 3.1 | — | 7.3 | 1.3 |
| 10 | 270 | 0.89 | 15 | 300 | 96 | 4 | 86 | 0.35 | 1.8 | 0 | 3.5 | 0.1 |

A comparison of Examples 1 and 4, shows that an increase in the reaction temperature from 240° C. to 270° C. substantially increases the glycerol-conversion rate (from 60 to 99.4%), although at the cost of a certain drop in selectivity towards the production of 1,2-propandiol.

From an examination of Examples 1–3, in which the parameter varied was the atomic ratio between the copper and the zinc in the catalyst, it can be seen that the conversion rates were always greater than 90% with a maximum when the atomic ratio between the copper and the zinc was 1.5. Selectivity towards 1,2-propandiol was always greater than 80% and the only other reaction product present in appreciable quantities was 1,2-ethandiol.

It is clear from a comparison of Examples 1, 5 and 6, that neither the conversion rate nor the selectivity are changed appreciably by a change in the concentration of the glycerol.

An increase in the quantity of the catalyst (Examples 7 to 9) increases the overall glycerol-conversion rate with a slight drop in selectivity towards 1,2-propandiol, which nevertheless remains greater than 80% in all cases. Finally, with crude glycerol which had been treated on an ion-exchange resin, a conversion rate of which lasts for several hours, it is important to prevent the temperature from exceeding 170° in any part of the reactor. When all the copper had been reduced, the nitrogen/hydrogen gas stream was replaced by a stream solely of hydrogen for about two hours.

At this point, it was possible to carry out the actual reaction proper by the supply to the reactor of a stream of hydrogen, saturated with injected water therein, and of an aqueous solution including 50% by weight of glycerol (reagent quality). The two streams were mixed in the Berl saddle layer as they entered the reactor so that the concentration of the glycerol upon admission to the catalytic bed was 30% by weight. The molar ratio of hydrogen to glycerol was 4 to 1. The operating pressure in the reactor was 15 MPa.

At the output of the reactor, the two streams of liquid and of gas were separated in a high-pressure separator and analysed by methods similar to those indicated with reference to the examples carried out discontinuously and described above.

Table II summarises the process conditions as regards the temperature and the space velocity (LHSV meaning the ratio between the hourly flow of liquid and the volume of the catalyst), and the results of the tests carried out, expressed according to the criteria set out above.

TABLE II

| EXAMPLE | T (°C.) | LHSV (h⁻¹) | CONV (%) | SELECTIVITY (%) | | | | |
|---|---|---|---|---|---|---|---|---|
| | | | | EG | PG | AL | A | GAS |
| 11 | 230 | 1,6 | 94.6 | 6,9 | 89 | 0,08 | 1,1 | 0,02 |
| 12 | 250 | 1,6 | 96,6 | 6,2 | 91 | 0,18 | 2,2 | 0,03 |
| 13 | 265 | 1,6 | 99,4 | 4,8 | 78 | 0,25 | 3,2 | 0,02 |
| 14 | 230 | 1 | 93,2 | 6,3 | 94 | 0 | 1,7 | 0 |
| 15 | 250 | 1 | 99,1 | 6 | 88 | 0 | 2 | 0,012 |
| 16 | 265 | 1 | 99,6 | 5,3 | 81 | 0,1 | 2,8 | 0,02 |

It is clear from a comparison of the tests carried out that, as in the discontinuous tests, the conversion rate increases as the temperature increases from 230° to 265°, with a slight decrease in selectivity towards 1,2-propandiol. Moreover, it was noted that a change in the space velocity does not appreciably change the test results (Examples 11-13 compared with examples 14-16).

What is claimed is:

1. A catalytic method of hydrogenating glycerol in order to produce a product comprising 1, 2-propandiol and 1,2- ethandiol, wherein glycerol is reacted with hydrogen in the presence of a catalyst comprising copper and zinc, at a temperature above 200° C. and a pressure of between 5 and 20 MPa.

2. A method according to claim 1, wherein the catalyst comprises a copper oxide/zinc oxide/alumina mixture in which the atomic ratio between the copper and the zinc is between 0.2 and 6.

3. A method according to claim 1, wherein the reaction is carried out at a temperature of between 220° and 280° C.

4. A method according to claim 3, wherein the reaction is carried out a temperature of between 230° and 265° C.

5. A method according to claim 1, wherein the glycerol is in an aqueous solvent and its concentration is from 20 to 60% by weight.

6. A method according to claim 1, wherein the glycerol is in an alcoholic solvent.

7. A method according to claim 1, wherein the glycerol used is impure glycerol resulting from the saponification or transesterification of fats.

* * * * *